(12) United States Patent
Kanemaru et al.

(10) Patent No.: US 7,011,829 B2
(45) Date of Patent: Mar. 14, 2006

(54) TISSUE FILLER

(76) Inventors: Shin-ichi Kanemaru, Park Haimu Sanadayama-koen 306, 3-3, Karahori-cho, Tennouji-ku, Osaka-shi, Osaka 543-0012 (JP); Tatsuo Nakamura, 46-10, Yoshida Kaguraoka-cho, Sakyo-ku, Kyoto-shi, Kyoto 606-8311 (JP); Hisayoshi Kojima, 13-26,Oomiya Yakushiyamahigashi-cho, Kita-ku, Kyoto-shi, Kyoto 603-8474 (JP); Yasuhiko Shimizu, 39-676, Kohata-ogurayama, Uji-shi, Kyoto 611-0002 (JP)

( * ) Notice: Subject to any disclaimer, the term of this patent is extended or adjusted under 35 U.S.C. 154(b) by 215 days.

(21) Appl. No.: 10/380,642

(22) PCT Filed: May 18, 2001

(86) PCT No.: PCT/JP01/04145

§ 371 (c)(1),
(2), (4) Date: Mar. 14, 2003

(65) Prior Publication Data

US 2004/0028659 A1    Feb. 12, 2004

(51) Int. Cl.
    *A01N 63/00*    (2006.01)

(52) U.S. Cl. .................... 424/93.7; 435/366; 435/372; 435/397; 623/11

(58) Field of Classification Search ................ 435/372, 435/366, 397; 424/93.7; 623/11
See application file for complete search history.

(56) References Cited

U.S. PATENT DOCUMENTS

| 4,592,864 A |   | 6/1986 | Miyata et al. |
| 4,695,281 A | * | 9/1987 | Miyata et al. ............ 623/23.72 |
| 5,855,619 A | * | 1/1999 | Caplan et al. ............ 623/23.72 |
| 6,623,963 B1 | * | 9/2003 | Muller et al. ................ 435/395 |

FOREIGN PATENT DOCUMENTS

| EP |   | 0132979 A2 | * | 2/1985 |
| JP |   | 07-097714 A |   | 4/1995 |
| WO |   | WO 97/40137 A1 |   | 10/1997 |
| WO |   | WO 00/47130 A1 |   | 8/2000 |

* cited by examiner

*Primary Examiner*—Leon B. Lankford, Jr.
(74) *Attorney, Agent, or Firm*—Frishauf, Holtz, Goodman & Chick, P.C.

(57) ABSTRACT

Disclosed are a tissue filler and tissue reconstruction method using the same that enables missing or reduced tissue of a body to recover to a normal state thereof, and the tissue filler comprised by mixing mesenchymal stem cells into a hydrochloric acid solution of atherocollagen.

3 Claims, No Drawings

TISSUE FILLER

This application is a United States National Phase application of International Application No. PCT/JP01/04145 (not published in English) filed May 18, 2001.

TECHNICAL FIELD

The present invention relates to a filler for missing or reduced tissue, and to a tissue reconstruction method using said tissue filler.

BACKGROUND ART

There are many patients suffering from disfunction of their organs caused by missing or reduced (atrophied) tissue, an example of which is the larynx.

The larynx is an important organ involved in the respiration, phonation and swallowing. In particular, deformation of the vocal cords brought about by lesions occurring thereon caused by cancer and other diseases, as well as their treatment and so forth, can cause phonation and swallowing disorders. These sequelae may be quite serious even after the primary disease has been completely treated.

In addition, deformation of the vocal cords is also caused by aging and excessive phonation.

This deformation is typically represented by, for example, partial defect, depression, atrophy or fibrous changes of the vocal cords. It prevents the vocal cords from complete closing during phonation and swallowing, and causes leakage of the air and misswallowing.

In the case of excessive leakage of the air, a large vital capacity is required for phonation, resulting in extremely hoarse voice and indistinct pronunciation, and creating a serious obstacle to social life due to impaired communication.

A treatment method consisting of injecting only collagen into peripheral tissue has been utilized for this tissue atrophy or arcuate deformation (and is used clinically for removal of skin wrinkles and vocal cord reconstruction).

However, since injected collagen is absorbed and eliminated in the body after about one month, in the case of the vocal cords, they return to their state prior to injection in an extremely short period of time, thereby preventing satisfactory phonation and prevention of misswallowing from being maintained.

In addition, frequency injection of collagen into the vocal cords places a considerable burden on the patient psychologically, physically and even financially.

DISCLOSURE OF THE INVENTION

Considering the improvement of the above circumstances, the object of the present invention is to provide a tissue filler and tissue reconstruction method using the same that enables the missing or reduced tissue to recover to a normal state.

The present invention is a tissue filler comprised by mixing mesenchymal stem cells into a hydrochloric acid solution of atherocollagen.

BEST MODE FOR CARRYING OUT THE INVENTION

To begin with, with respect to the raw materials, various types of collagen that have been used in the past can still be used in the present invention. Examples of these collagen include neutral solubilized, acid-solubilized, alkaline-solubilized and enzyme-solubilized collagen. Among them, enzyme-solubilized collagen that has been treated with an enzyme such as pepsin, trypsin, chymotrypsin, papain or pronase is preferable. This is because the telopeptides functioning as antigenic groups in the collagen molecule are reliably removed, thereby making it possible to nearly completely eliminate antigenicity.

There are no particular restrictions on the origin of this collagen, and type I collagen or a mixture of type I collagen and type III collagen can be used after extracting and purifying from the skin, bone, cartilage, tendons or organs and so forth of animals such as cow, pig, rabbit, sheep, kangaroo, birds or fish.

On the other hand, with respect to the mesenchymal stem cells, cells are used from which hematopoietic cells have been removed by subculturing extracted bone marrow.

More specifically, bone marrow that has been extracted using a bone marrow puncture needle from the sternum, ilium or long tubular bone and so forth of a donor (preferably the patient him or herself due to immunity consideration) is cultured and grown using a primary cell culturing with, for example, Eagle's Minimum Essential Medium (Eagle's MEM) containing 10% FBS (fetal bovine serum). (In the case of using a culture bottle, (floating) hematopoietic cells are removed in the process of replacing the culture medium, while (adherent) mesenchymal stem cells increase in about 1 week on the bottom of said culture bottle. Cultured cells were observed microscopically, and at the point of confluent growth, the cells are separated from the bottom thereof using an enzyme (trypsin). The collected cell suspension is confirmed for the number of cells by placing to an ordinary cell counter such as the Metallized Counting Chamber (manufactured by Becton Dickinson). Furthermore, roughly $10^5$–$10^7$ cells can be collected from a medium-size culture bottle (260 ml).

The tissue filler of the present invention is obtained by mixing mesenchymal stem cells (suspension) prepared in the manner described above into a hydrochloric acid solution of the aforementioned collagen also prepared in the manner described above to a predetermined number of cells ($10^5$–$10^7$ cells/ml collagen).

Application to patients should be carried out by aspirating the above collagen-stem cell mixture into a small syringe (roughly 1 ml), and locally injecting into the target tissue with a roughly 27G narrow injection needle or catheter needle. (Furthermore, in the case of using a large needle such as a roughly 21G or 18G needle, caution is required since said collagen-stem cell mixture may flow back from the needle hole.)

TEST EXAMPLE 1

Two ml of bone marrow were aspirated and extracted by bone marrow puncture from the femur of a general anesthetized adult beagle dog (body weight: 10 kg). The extracted bone marrow was then mixed with 10 ml of Eagle's MEM containing 10% FBS (fetal bovine serum), placed in a culture bottle (260 ml), and then cultured in a carbon dioxide gas incubator. The culture medium was exchanged after 4 days, after 1 week and after 10 days. Suspended hematopoietic stem cells and so forth were removed by this procedure, and only adhering cells (namely, mesenchymal stem cells) remained on the bottom of said bottle. In the second week, microscopically, the cultured cells were confirmed to have grown on the whole surface of the bottom of said bottle, then were separated from the bottom thereof with a method using trypsin. The number of cells was counted with a Metallized Counting Chamber (manufactured by Becton Dickinson), there were determined to be $3 \times 10^6$ cells.

After thoroughly washing the separated cells with phosphate-buffered saline (PBS) to remove the trypsin, they were concentrated with a centrifuge (cell concentration: $3 \times 10^6$ cells/0.5 ml).

One ml of a hydrochloric acid solution of enzyme-solubilized collagen obtained from pigskin (pH=3, collagen concentration=1.0 wt %, manufactured by Nippon Meat Packers) was mixed with said concentrated cells in a culture dish. The collagen solution containing mesenchymal stem cells originating in bone marrow maintained its mass form even following addition of Eagle's MEM.

The collagen mass immersed in this culture medium was again cultured in a carbon dioxide gas incubator. The culture medium was exchanged every 5 days. As a result of subsequent microscopic observation, said cells were confirmed to continue to be viable within collagen that maintained a three-dimensional structure not only 1 week later, but also 2 weeks later. It was also confirmed that the cells, which had been spherical immediately after the start of culturing, grew while undergoing differentiation such as forming projections and becoming a fusiform shape, while some of the cells were also confirmed to spread to the bottom of the culture dish.

Portions of the collagen+cell mixture were taken immediately after the start of culturing, 1 week and 2 weeks later, respectively, with a teaspoon, embedded in resin and prepared into 10 $\mu$m thin sections followed by staining with hematoxylin and eosin stain and observing with a light microscope. The cells were confirmed to be embedded into the collagen, and their number had increased over time, indicating that collagen exhibits a high degree of affinity with mesenchymal stem cells.

TEST EXAMPLE 2

Two ml of bone marrow were respectively extracted by bone marrow puncture from the femora (which can alternatively change to humeri) of general anesthetized adult beagle dogs (body weights: 8–15 kg, 10 animals). The extracted bone marrow was then mixed with 10 ml of Eagle's MEM containing 10% FBS (fetal bovine serum), placed in culture bottles (260 ml), and then cultured in a carbon dioxide gas incubator. The culture medium was exchanged after 4 days, after 1 week and every 5 days thereafter. (Suspended hematopoietic stem cells and so forth were removed by this procedure, and only mesenchymal stem cells remained). The bottoms of said bottles were covered with mesenchymal stem cells in 2 weeks to 1.5 months. Said cells were separated from said bottoms thereof with a method using trypsin, and thoroughly washed with PBS to remove the trypsin. The amount of 0.5 ml of a concentrated suspension of these cells (concentrated by using a centrifuge, cell count=$2 \times 10^6$ to $3 \times 10^6$ cells/10 ml) were stained with 1 ml of FM-Dil fluorescent pigment (manufactured by Molecular Probe). One ml of a hydrochloric acid solution of collagen (same as in Test Example 1) and said concentrated cells were mixed in a culture dish.

After aspirating 1 ml of said mixture into a 1 ml plastic syringe, a 27 G catheter needle (length: 4 cm) was provided to said syringe.

The dogs from which the bone marrow cells were extracted were again subjected to general anesthesia, their mouths were opened, and while observing with a Macintosh laryngoscope, about 0.5 ml each of said collagen+cell mixture were injected with said syringe into the left vocal cord. A control group was injected with the same amount of said collagen hydrochloric acid solution only into the right vocal cord.

Changes in the vocal cord after injection were observed over time using a bronchial endoscopic system (CLV-U40D, manufactured by Olympus Optical).

Although the left vocal cord was distended immediately after injection, and remained distended 2 weeks and even 4 weeks later, the distension of the right vocal cord gradually decreased, and had returned to nearly the same state as before injection in week 4.

Each of the animals was sacrificed after 2 and 4 weeks, the larynx was immediately excised, and the left and right vocal cords were frozen in Tissue-Tek OCT Compound followed by the preparation of frozen sections (thickness=15 $\mu$m) using a cryostat frozen thin slicer (MH500M).

Each section was observed using a fluorescent microscope (IX70, manufactured by Olympus Optical). Cells that emitted fluorescence were observed in the vocal cords of the collagen+cell mixture group in weeks 2 and 4, and connective tissue had formed around them. On the other hand, although a small amount of extracellular substance thought to be the injected collagen was observed in week 2 in the control group, there were no cells that were observed to emit fluorescence, absorption of collagen was observed in week 4, and body tissue at the injected site again become reduced.

Although the explanation thus far has focused primarily on the vocal cords as the target tissue, since the tissue filler and tissue reconstruction method using the same of the present invention utilizes a mechanism in which mesenchymal stem cells, which have an auto-growth function and are injected into the target tissue with collagen, remain in said tissue by using collagen as a scaffold, and a portion of those cells grow to regenerate said tissue to nearly a normal state, while the collagen itself is degraded and absorbed by said tissue in roughly 1 month, the present invention can also be applied to tissue other than vocal cords, examples of which include tissue that has been lost due to removal of cancer, mammae, palpebrae and directly beneath skin in which wrinkles have formed.

In addition, since the grown mesenchymal stem cells can be made to retain or preserve their inherent function by freeze-drying using liquid nitrogen, the tissue filler of the present invention may also be prepared by returning said preserved mesenchymal stem cells to the state of a cell suspension prior to surgery and mixing them with a hydrochloric acid solution of collagen prepared separately. Furthermore, storage of said grown mesenchymal stem cells in small vessels such as ampules is convenient for use.

INDUSTRIAL APPLICABILITY

According to the tissue filler and tissue reconstruction method using the same of the present invention, different kinds of missing or reduced (atrophied) tissue and the form of its peripheral tissue can be reconstructed to a nearly normal state.

What is claimed is:

1. A method for vocal cord tissue reconstruction comprising injecting into the vocal cord tissue of a patient a filler which comprises a hydrochloric acid solution of atherocollagen and mesenchymal stem cells wherein the mesenchymal stem cells were grown and purified by subculturing the patient's own bone marrow.

2. The method according to claim 1, wherein said mesenchymal stem cells are contained in an amount of $10^5$–$10^7$ cells/ml of said hydrochloric acid solution of atherocollagen.

3. The method according to claim 1, wherein said mesenchymal stem cells, after being grown and purified, are stored using a frozen storage liquid and liquid nitrogen, and said filler is prepared by mixing a cell suspension obtained by thawing said stored mesenchymal stem cells with said hydrochloric acid solution of atherocollagen prior to a surgery.

* * * * *